United States Patent [19]
Wolf et al.

[11] Patent Number: 5,480,805
[45] Date of Patent: Jan. 2, 1996

[54] COMPOSITION FOR MODULATING STEROLS IN YEAST

[75] Inventors: Fred R. Wolf, Naperville; Richard E. Cuellar, Glen Ellyn, both of Ill.

[73] Assignee: Amoco Corporation, Naperville, Ill.

[21] Appl. No.: 240,496

[22] Filed: May 10, 1994

Related U.S. Application Data

[63] Continuation of Ser. No. 929,764, Aug. 12, 1992, abandoned.

[51] Int. Cl.⁶ ............................ C12N 15/61; C12N 15/81; C12N 1/19
[52] U.S. Cl. ...................... 435/320.1; 530/371; 536/23.2; 536/23.74; 435/52; 435/53; 435/71.1; 435/171; 435/252.3; 435/233; 935/60; 935/69
[58] Field of Search ......................... 530/371; 536/23.2, 536/23.74; 435/52, 53, 71.1, 171, 252.3, 233, 320.1; 935/60, 69

[56] References Cited

PUBLICATIONS

Ashman et al. 1991 (week of 16 Aug.) Lipids 26 (8):628–632.
Arthington et al. 1991 (30 Oct.) Gene 107(1):173–174.
Rose 1987 In Methods in Enzymology 152; 481–504.
Bard et al. 1990 Inform 1(4):324–325 (Abstract, EE5).

*Primary Examiner*—Patrica R. Moody
*Attorney, Agent, or Firm*—Norval B. Galloway

[57] ABSTRACT

A structural gene encoding a polypeptide with Δ8-7 sterol isomerase activity is disclosed, Recombinant DNA molecules useful for transforming yeast and mutant yeast transformed with such recombinant DNA molecules are also disclosed. The structural gene is useful for modulating the accumulation of sterols in yeast comprising increasing the expression level of a structural gene encoding a polypeptide having Δ8-7 sterol isomerase activity in a mutant yeast having single or double defects in the expression of sterol biosynthetic enzymes is provided.

7 Claims, 7 Drawing Sheets

```
-378        -370         -360
   AGATAGAG CTTCTATAGA AGTACAGKTA
-350        -340         -330
   TTCAAACAAA AAAAAAAAAA AAAACAAGGG
-320        -310         -300
   TTGTGGAGTA TGCCACTAGC AGTCTGCTAT
-280        -280         -270
   GTTGATTCTG NCTTANTTAN TCAACSRARN
-260        -250         -240
   NNATCCCATT ATGATCTTAT GCAATGCACA
-230        -220         -210
   TTSCTGCCCT TACGCTCCAG GGCASWWYCG
-200        -190         -180
   AACCACGGCC CTCGTATAAG CCGCAAGGAA
-170        -160         -150
   AACTACCGGT GCTATCGTTC TCSKTTGGAT
-140        -130         -120
   GATTTTCAGT ATRGAAGNAA TTTGGATAGA
-110        -100         -90
   NNTCKRCAGC GCCATGGTAT ATAAGAGAAA
-80         -70          -60
   GAAGCGGTAA CGTTTGACAC TGGGTTCAGA
-50         -40          -30
   TCTCTCTTGT CGCTCAATCA AACTAAGACT
-20         -10
   AGCCCNAGAC CATTATAGCC
```

FIG. 2A

```
            10                    20                    30
ATG AAG TTT TTC CCA CTC CTT TTG TTG ATT
Met Lys Phe Phe Pro Leu Leu Leu Leu Ile
                 5                                      10

40                    50                    60
GGT GTT GTA GGC TAC ATT ATG AAC GTA TTG
Gly Val Val Gly Tyr Ile Met Asn Val Leu
                15                                      20

70                    80                    90
TTC ACT ACC TGG TTG CCA ACC AAT TAC ATG
Phe Thr Thr Trp Leu Pro Thr Asn Tyr Met
                25                                      30

100                   110                   120
TTC GAT CCA AAA ACT TTG AAC GAA ATA TGT
Phe Asp Pro Lys Thr Leu Asn Glu Ile Cys
                35                                      40

130                   140                   150
AAC TCG GTG ATT AGC AAA CAC AAC GCA GCA
Asn Ser Val Ile Ser Lys His Asn Ala Ala
                45                                      50

160                   170                   180
GAA GGT TTA TCC ACT GAA GAC CTG TTA CAG
Glu Gly Leu Ser Thr Glu Asp Leu Leu Gln
                55                                      60

190                   200                   210
GAT GTC AGA GAC GCA CTT GCC TCT CAT TAC
Asp Val Arg Asp Ala Leu Ala Ser His Tyr
                65                                      70

220                   230                   240
GGG GAC GAA TAC ATC AAC AGG TAC GTC AAA
Gly Asp Glu Tyr Ile Asn Arg Tyr Val Lys
                75                                      80
```

FIG. 2B

```
                    250                 260                 270
        GAA GAA TGG GTC TTC AAC AAT GCT GGT GGT
        Glu Glu Trp Val Phe Asn Asn Ala Gly Gly
                         85                              90

280                 290                 300
        GCG ATG GGC CAA ATG ATC ATC CTA CAC GCT
        Ala Met Gly Gln Met Ile Ile Leu His Ala
                         95                             100

310                 320                 330
        TCC GTA TCC GAG TAC TTA ATT CTA TTC GGA
        Ser Val Ser Glu Tyr Leu Ile Leu Phe Gly
                        105                             110

340                 350                 360
        ACC GCT GTT GGT ACT GAA GGG CAC ACA GGT
        Thr Ala Val Gly Thr Glu Gly His Thr Gly
                        115                             120

370                 380                 390
        GTT CAC TTT GCT GAC GAC TAT TTT ACC ATC
        Val His Phe Ala Asp Asp Tyr Phe Thr Ile
                        125                             130

400                 410                 420
        TTA CAT GGT ACG CAA ATC GCA GCA TTG CCA
        Leu His Gly Thr Gln Ile Ala Ala Leu Pro
                        135                             140

430                 440                 450
        TAT GCC ACT GAA GCC GAA GTT TAC ACT CCT
        Tyr Ala Thr Glu Ala Glu Val Tyr Thr Pro
                        145                             150

460                 470                 480
        GGT ATG ACT CAT CAC TTG AAG AAG GGA TAC
        Gly Met Thr His His Leu Lys Lys Gly Tyr
                        155                             160
```

FIG. 2C

```
            490             500             510
GCC AAG CAA TAC AGC ATG CCA GGT GGT TCC
Ala Lys Gln Tyr Ser Met Pro Gly Gly Ser
                165                     170

520             530             540
TTT GCC CTT GAA TTG GCT CAA GGC TGG ATT
Phe Ala Leu Glu Leu Ala Gln Gly Trp Ile
                175                     180

550             560             570
CCA TGT ATG TTG CCA TTC GGG TTT TTG GAC
Pro Cys Met Leu Pro Phe Gly Phe Leu Asp
                185                     190

580             590             600
ACT TTC TCC AGT ACT CTT GAT TTA TAC ACT
Thr Phe Ser Ser Thr Leu Asp Leu Tyr Thr
                195                     200

610             620             630
CTA TAT AGA ACT GTC TAC CTG ACT GCC AGG
Leu Tyr Arg Thr Val Tyr Leu Thr Ala Arg
                205                     210

640             650             660
GAC ATG GGT AAG AAC TTG TTG CAA AAC AAA
Asp Met Gly Lys Asn Leu Leu Gln Asn Lys
                215                     220

670
AAG TTC TAA
Lys Phe END
        222
```

FIG. 2D

```
                670         680         690
                  G CTGCCCGACC TCACGAAATC
                700         710         720
         AGTCATGCGG TAGTCCATTA TAATATAACT
                730         740         750
         ATTATTATTA TTACTATTAC TATTATTATT
                760         770         780
         ATTATTATTA TTATTATCTA TTGTTTATAT
                790         800         810
         CTCTTTAGCT TTTTATCACC TACGACGACG
                820         830         840
         GATATATCGG CGTTTGCAAA GTGAAAGGCG
                850         860         870
         TCTTGGTGGA CATGAACTCA ATCTTCAATT
                880         890         900
         CTTTGAAAGC GGTGTATGGC GTATAAGGCC
                910         920         930
         TTNAASSATC GTGCAAACAN TAAMKACNKC
                940         950         960
         NNSAATMANN GNYSTGNRCA NNNCNNCANN
                970         980         990
         NACTCNNWTA GCAAGNNGCC TCNTNANNAN
               1000        1010        1020
         NNCCCTCATC CCGGCCCTTT CTCCTTTGAC
               1030        1040        1050
         TGCGAAGCAA TCCAAGGGAA TTTCTTCTCC
               1060        1070        1080
         TCAAACCCAA TATCTAGCTT TGTTGTGGAT
               1090        1100        1110
         ACGTACAAAC AATTGCATTC TCACAGACAA
               1120        1130
         TCTTTGGAGC TGGTCAATCC
```

FIG. 2E

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1508 base pairs
        ( B ) TYPE: nucleic acid
        ( C ) STRANDEDNESS: double
        ( D ) TOPOLOGY: linear 5,480,805

( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 379..1047

( x i ) SEQUENCE DESCRIPTION: SEQ ID NO:1:

```
AGATAGAGCT   TCTATAGAAG   TACAGKTATT   CAAACAAAAA   AAAAAAAAAA   AACAAGGGTT     60
GTGGAGTATG   CCACTAGCAG   TCTGCTATGT   TGATTCTGNC   TTANTTANTC   AACSRARNNN    120
ATCCCATTAT   GATCTTATGC   AATGCACATT   SCTGCCCTTA   CGCTCCAGGG   CASWWYCGAA    180
CCACGGCCCT   CGTATAAGCC   GCAAGGAAAA   CTACCGGTGC   TATCGTTCTC   SKTTGGATGA    240
TTTTCAGTAT   RGAAGNAATT   TGGATAGANN   TCKRCAGCGC   CATGGTATAT   AAGAGAAAGA    300
AGCGGTAACG   TTTGACACTG   GGTTCAGATC   TCTCTTGTCG   CTCAATCAAA   CTAAGACTAG    360
CCCNAGACCA   TTATAGCCAT   GAAGTTTTTC   CCACTCCTTT   TGTTGATTGG   TGTTGTAGGC    420
TACATTATGA   ACGTATTGTT   CACTACCTGG   TTGCCAACCA   ATTACATGTT   CGATCCAAAA    480
ACTTTGAACG   AAATATGTAA   CTCGGTGATT   AGCAAACACA   ACGCAGCAGA   AGGTTTATCC    540
ACTGAAGACC   TGTTACAGGA   TGTCAGAGAC   GCACTTGCCT   CTCATTACGG   GGACGAATAC    600
ATCAACAGGT   ACGTCAAAGA   AGAATGGGTC   TTCAACAATG   CTGGTGGTGC   GATGGGCCAA    660
ATGATCATCC   TACACGCTTC   CGTATCCGAG   TACTTAATTC   TATTCGGAAC   CGCTGTTGGT    720
ACTGAAGGGC   ACACAGGTGT   TCACTTTGCT   GACGACTATT   TTACCATCTT   ACATGGTACG    780
CAAATCGCAG   CATTGCCATA   TGCCACTGAA   GCCGAAGTTT   ACACTCCTGG   TATGACTCAT    840
CACTTGAAGA   AGGGATACGC   CAAGCAATAC   AGCATGCCAG   GTGGTTCCTT   TGCCCTTGAA    900
TTGGCTCAAG   GCTGGATTCC   ATGTATGTTG   CCATTCGGGT   TTTTGGACAC   TTTCTCCAGT    960
ACTCTTGATT   TATACACTCT   ATATAGAACT   GTCTACCTGA   CTGCCAGGGA   CATGGGTAAG   1020
AACTTGTTGC   AAAACAAAAA   GTTCTAAGCT   GCCCGACCTC   ACGAAATCAG   TCATGCGGTA   1080
GTCCATTATA   ATATAACTAT   TATTATTATT   ACTATTACTA   TTATTATTAT   TATTATTATT   1140
ATTATCTATT   GTTTATATCT   CTTTAGCTTT   TTATCACCTA   CGACGACGGA   TATATCGGCG   1200
TTTGCAAAGT   GAAAGGCGTC   TTGGTGGACA   TGAACTCAAT   CTTCAATTCT   TTGAAAGCGG   1260
TGTATGGCGT   ATAAGGCCTT   NAASSATCGT   GCAAACANTA   AMKACNKCNN   SAATMANNGN   1320
YSTGNRCANN   NCNNCANNNA   CTCNNWTAGC   AAGNNGCCTC   NTNANNANNN   CCCTCATCCC   1380
GGCCCTTTCT   CCTTTGACTG   CGAAGCAATC   CAAGGGAATT   TCTTCTCCTC   AAACCCAATA   1440
TCTAGCTTTG   TTGTGGATAC   GTACAAACAA   TTGCATTCTC   ACAGACAATC   TTTGGAGCTG   1500
GTCAATCC                                                                    1508
```

( 2 ) INFORMATION FOR SEQ ID NO:2:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Lys Phe Phe Pro Leu Leu Leu Leu Ile Gly Val Val Gly Tyr Ile
 1               5                   10                      15

Met Asn Val Leu Phe Thr Thr Trp Leu Pro Thr Asn Tyr Met Phe Asp
            20                  25                  30

Pro Lys Thr Leu Asn Glu Ile Cys Asn Ser Val Ile Ser Lys His Asn
        35              40              45

Ala Ala Glu Gly Leu Ser Thr Glu Asp Leu Leu Gln Asp Val Arg Asp
    50              55              60

Ala Leu Ala Ser His Tyr Gly Asp Glu Tyr Ile Asn Arg Tyr Val Lys
65              70                  75                      80

Glu Glu Trp Val Phe Asn Asn Ala Gly Gly Ala Met Gly Gln Met Ile
                85              90                  95

Ile Leu His Ala Ser Val Ser Glu Tyr Leu Ile Leu Phe Gly Thr Ala
            100             105                     110

Val Gly Thr Glu Gly His Thr Gly Val His Phe Ala Asp Asp Tyr Phe
        115             120                 125

Thr Ile Leu His Gly Thr Gln Ile Ala Ala Leu Pro Tyr Ala Thr Glu
    130             135                 140

Ala Glu Val Tyr Thr Pro Gly Met Thr His His Leu Lys Lys Gly Tyr
145             150                 155                     160

Ala Lys Gln Tyr Ser Met Pro Gly Gly Ser Phe Ala Leu Glu Leu Ala
                165                 170                 175

Gln Gly Trp Ile Pro Cys Met Leu Pro Phe Gly Phe Leu Asp Thr Phe
            180                 185                 190

Ser Ser Thr Leu Asp Leu Tyr Thr Leu Tyr Arg Thr Val Tyr Leu Thr
        195             200                 205

Ala Arg Asp Met Gly Lys Asn Leu Leu Gln Asn Lys Lys Phe
    210             215                 220
```

COMPOSITION FOR MODULATING STEROLS IN YEAST

This is a continuation of application Ser. No. 07/929,764, filed on Aug. 12, 1992,(now abandoned).

DESCRIPTION

1. Technical Field

The present invention relates to the isolation, characterization and expression of the structural genes from *Saccharomyces cerevisiae* encoding a polypeptide having Δ8-7 isomerase activity toward sterols. The invention also relates to a method for increasing the accumulation of specific sterols in yeast. Sterol accumulation is increased by increasing the expression level of a gene encoding a polypeptide having Δ8-7 isomerase activity.

2. Background of the Invention

As used herein, the term "sterol" refers to derivatives of a fused, reduced ring system, cyclopenta-[α]-phenanthrene, comprising three fused cyclohexane rings (A, B and C) in a phenanthrene arrangement, and a terminal cyclopentane ring (D) having the formula and carbon atom position numbering shown below:

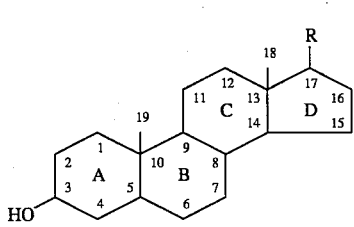

where R is an 8 to 10 carbon-atom sidechain.

Sterols are metabolically derived from acetate. Acetyl coenzyme A (CoA) reacts with acetoacetyl CoA to form 3-hydroxy-3-methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

In yeast, squalene is converted to squalene epoxide, which is then cyclized to form lanosterol. Lanosterol has two methyl groups at position 4, a methyl group at position 14, a double bond at position 8(9) and an 8 carbon sidechain of the formula: $CH_3CH(CH_2)_2CH=C(CH_3)_2$.

Lanosterol is sequentially demethylated at positions 14 and 4 to form zymosterol (cholesta-8,24-dienol), which is converted to ergosterol (ergosta- 5,7,22-trienol), the most abundant sterol of naturally occurring, wild-type yeast via a series of five enzymatic reactions schematically diagramed in FIG. 1.

The five reactions are:

a. methylation of the carbon at position 24, catalyzed by a 24-methyltransferase;

b. movement of the double bond at position 8(9) to position 7(8), catalyzed by a Δ8-7 isomerase;

c. introduction of a double bond at position 5(6), catalyzed by a 5-dehydrogenase (desaturase);

d. introduction of a double bond at position 22(23), catalyzed by a 22-dehydrogenase (desaturase); and e. removal of a double bond at position 24(28), catalyzed by a 24(28)-hydrogenase (reductase).

In wild-type yeast of the species *Saccharomyces cerevisiae* (*S. cerevisiae*), the predominant order of these reactions is thought to be a, b, c, d and e. [Parks et al., *CRC Critical Reviews in Microbiology*, 6:301–341 (1978)].

According to such a predominant pathway, zymosterol is converted sequentially to fecosterol [ergosta-8,24(28)-dienol], episterol [ergosta- 7,24(28)-dienol], ergosta-5,7, 24(28)-trienol, ergosta-5,7,22, 24(28)-tetraenol, and finally ergosterol.

If the enzymes catalyzing the reactions involved in the predominant pathway are substrate specific, then one would expect to find only the six sterols set forth above in yeast. Such, however, is not the case. Eighteen sterols have been found and described. [See, e.g., Parks et al., *CRC Critical Reviews in Microbiology*, 6:301–341 (1978); Woods, R. A. et. al., *Microbios*, 10(A):73–80 (1974); Bard, M. et al., *Lipids*, 12:645–654 (1977) (See Table 1)]. Thus, at least some of The enzymes are not substrate specific.

TABLE 1

| | Sterol | Required* Enzymes |
|---|---|---|
| 1. | Zymosterol (cholesta-8,24-dienol) | none |
| 2. | fecosterol (ergosta-8,24(28)-dienol) | a |
| 3. | episterol (ergosta-7,24(28)-dienol) | a,b |
| 4. | ergosta-5,7,24(28)-trienol | a,b,c |
| 5. | ergosta-5,7,22,24(28)-tetraenol | a,b,c,d |
| 6. | ergosterol (ergosta-5,7,22-trienol) | a,b,c,d,e |
| 7. | ergosta-7,22,24(28)-trienol | a,b,d |
| 8. | cholesta-7,24-dienol | b |
| 9. | cholesta-5,7,24-trienol | b,c |
| 10. | cholesta-5,7,22,24- tetraenol | b,c,d |
| 11. | ergosta-5,7-dienol | a,b,c,e |
| 12. | ergosta-7,22-dienol | a,b,d,e |
| 13. | ergosta-7-enol | a,b,e |
| 14. | ergosta-5,8-dienol | a,c,e |
| 15. | ergosta-5,8,22-trienol | a,c,d,e |
| 16. | ergosta-8,22-dienol | a,d,e |
| 17. | ergosta-8-enol | a,e |
| 18. | ergosta-8,14,24(28)-trienol | a |

*Enzymes theoretically required for the synthesis of the designated sterol.

Despite the lack of substrate specificity, one might expect that specific alterations in the sterol biosynthetic pathway would have predictable consequences. Currently available data show that such predictability is not present.

For example, mutant *S. cerevisiae* with a defect in Δ8-7 isomerase (enzyme b), designated erg2, might be expected to accumulate sterols 1–2, and 14–18. Parks et al., *CRC Critical Reviews in Microbiology*, 6:301–341 (1978) report that erg2 mutants accumulate only ergosta-5,8-dienol (#14), ergosta-8,22-dienol (#16), ergosta-5,8,22-trienol (#15), fecosterol (#2) and zymosterol (#1).

Mutant *S. cerevisiae* with a defect in the expression of zymosterol-24-methyl-transferase (enzyme a), which mutants are designated erg6, might be expected to accumulate sterols 1 and 8–10 of Table 1, which sterols theoretically do not require the action of enzyme a for their synthesis. Parks et al., *CRC Critical Reviews in Microbiology*, 6:301–341 (1978), however, report that erg6 mutants accumulate only zymosterol (#1), cholesta-5,7,24-trienol (#9) and cholesta-5,7,22,24-tetraenol (#10). Bard, M. et al., *Lipids*, 12:645–654 (1977), on the other hand, report that erg6 mutants accumulate only sterols #1 and #10.

Still further, mutant *S. cerevisiae* with a defect in the expression of ergosta-5,7,24(28)-trienol-22-dehydrogenase (enzyme d), designated erg5, might be expected to accumulate sterols 1–4, 6, 8, 9, 11, 13, 14, 17 and 18. Parks et al., *CRC Critical Reviews in Mircobiology*, 6:301–341 (1978) report, that erg5 mutants accumulate only ergosta-5,7-dienol (#11), ergosta- 5,7,24(28)-trienol (#4), ergosta-8,14,24(28)-trienol (#18) and episterol (#3). In contrast, Bard et al., *Lipids*, 12:645–654 (1977) report that erg5 mutants accumulate zymosterol (#1), ergosta-5,7-dienol (#11), ergosta-5, 7,24(28)-trienol (#4), ergosta-7,24(28)-dienol (#3) and ergosta-8,14,24(28)-trienol (#18).

These data, taken together, show that specific defects in the expression of one sterol synthetic enzyme do not lead to predictable changes in sterol accumulation. A similar degree of unpredictability is found when sterol accumulation is examined in mutants having two defects in enzymes of the sterol biosynthetic pathway.

Thus, for example, erg5-erg6 double mutants (defects in enzymes d and a) might be expected to accumulate sterols 1,8 and 9. Parks et. al. and Bard et al., above, report that erg5-erg6 double mutants accumulate only zymosterol (#1) and cholesta-5,7,24-trienol (#9).

These data relating to sterol accumulation in yeast show that specific alterations in enzyme activity do not result in predictable changes in sterol accumulation. The data further show a lack of agreement between different investigators studying identical alterations. The present invention provides a method and composition for increasing the accumulation of specific sterols in yeast, and consequently enhances the level of understanding of sterol biosynthesis.

SUMMARY OF THE INVENTION

The present invention provides an isolated DNA segment comprising a nucleotide sequence that contains at least about 669 base pairs that define a structural gene for expressing the *Saccharomyces cerevisiae* polypeptide having Δ8-7 activity toward sterols, hereafter referred to as Δ8-7 isomerase. The invention also contemplates variants and analogs of the structural gene as defined herein.

Another aspect of the present invention is a recombinant DNA molecule comprising a vector operatively linked to a DNA segment of the invention and a promoter suitable for driving the expression of the polypeptide in a compatible host organism.

The structural gene encoding a polypeptide having Δ8-7 isomerase activity preferably encodes an active, "core" Δ8-7 isomerase enzyme, which enzyme comprises the catalytic and at least a portion of a putative membrane associating region of Δ8-7 isomerase enzyme. The copy number of the structural gene in a yeast can be increased by transforming the yeast with a recombinant DNA molecule comprising a vector operatively linked to an exogenous DNA segment that encodes a polypeptide having Δ8-7 isomerase activity and a promoter that is suitable for driving the expression of the encoded polypeptide in the transformed yeast.

Suitable promoters include promoters that are subject to inducible regulation by factors either extrinsic or intrinsic to yeast. Preferably, both the promoter and the exogenous DNA segment are integrated into the chromosomal DNA of the transformed yeast.

The present invention also generally permits a method of modulating sterol composition and accumulation in yeasts. The invention is particularly advantageous with respect mutant yeasts having a single or double defect in the expression of sterol biosynthetic pathway enzymes. This method comprises transforming yeasts with a recombinant DNA molecule comprising a vector operatively linked to an exogenous DNA segment that encodes a polypeptide having catalytic activity and a promoter suitable for driving the expression of Δ8-7 isomerase in the transformed yeast.

The present invention most preferably permits a method of decreasing squalene and zymosterol, while increasing cholesta-7,24-dienol and cholesta-5,7,24-trienol accumulation in yeast of the species *S. cerevisiae* comprising increasing the expression level of a structural gene encoding a polypeptide having Δ8-7 isomerase activity in a mutant *S. cerevisiae* having defects in the expression of zymosterol-24-methyltransferase (erg6) and ergosta-5,7,24(28)-trienol-22-dehydrogenase (erg5).

Further, transformation of a mutant yeast having a defect in the expression of the enzyme episterol-5-dehydrogenase (erg 3) results in a transformed, mutant yeast which does not accumulate ergosta-8,22-dienol, ergosta-7,22-dienol, ergosta-8-enol and ergosta-7-enol. Transformation of a mutant yeast having a double defect in the expression of zymosterol-24-methyltransferase and episterol-5-dehydrogenase enzymes (erg6 and erg3) results in a transformed mutant yeast which overaccumulates squalene, zymosterol and cholesta-7,24-dienol. Transformation of a mutant yeast having a defect in the expression of ergosta-5,7,24(28)-trienol-22-dehydrogenase (erg 5) results in a transformed mutant yeast which overaccumulates zymosterol and a mixture of ergosta-5,7,24(28)-trienol and ergosta-5,7-dienol.

The present invention provides several benefits and advantages.

One advantage of the present invention is the provision of a gene which can be transformed into yeasts resulting in the predictable redistribution of specific sterols.

Another advantage of the present invention is the ability to accumulate desirable sterols to levels markedly greater than levels found in non-transformed yeast.

Still further benefits and advantages will be apparent to the skilled worker from the description that follows.

BRIEF DESCRIPTIONS OF THE DRAWINGS

FIG. 1 is a schematic diagram illustrating the various transformation steps involved in the metabolic conversion of zymosterol to ergosterol as shown and discussed in Bard et al., *Lipids*, 12(8):645 (1977). The letters (a–e) indicate the five enzymes responsible for catalyzing the individual transformation steps. Numerals alone or with the letter "C" and an enzymic name indicate the position of the enzymes' activities and the activity of each enzyme.

FIG. 2, is the composite nucleotide sequence of the Δ8-7 isomerase gene region (SEQ ID NOS: 1 and 2). Position 1 corresponds to the first nucleotide of the ATG triplet coding for the initiator methionine. The nucleotides on the 5' side of position 1 are indicated by negative numbers. The predicted amino acid sequence is shown below the nucleotide sequence. The amino acid residues are numbered (right-hand side) beginning with the initiator methionine.

FIG. 3 is a schematic diagram showing the physical structure and genetic organization of plasmid pARCml508. Certain restriction sites indicated by lines linked to the arcs and abbreviation for their respective restriction endonuclease enzymes are indicated.

DETAILED DESCRIPTION OF THE INVENTION

I. Definitions

Figure 1:
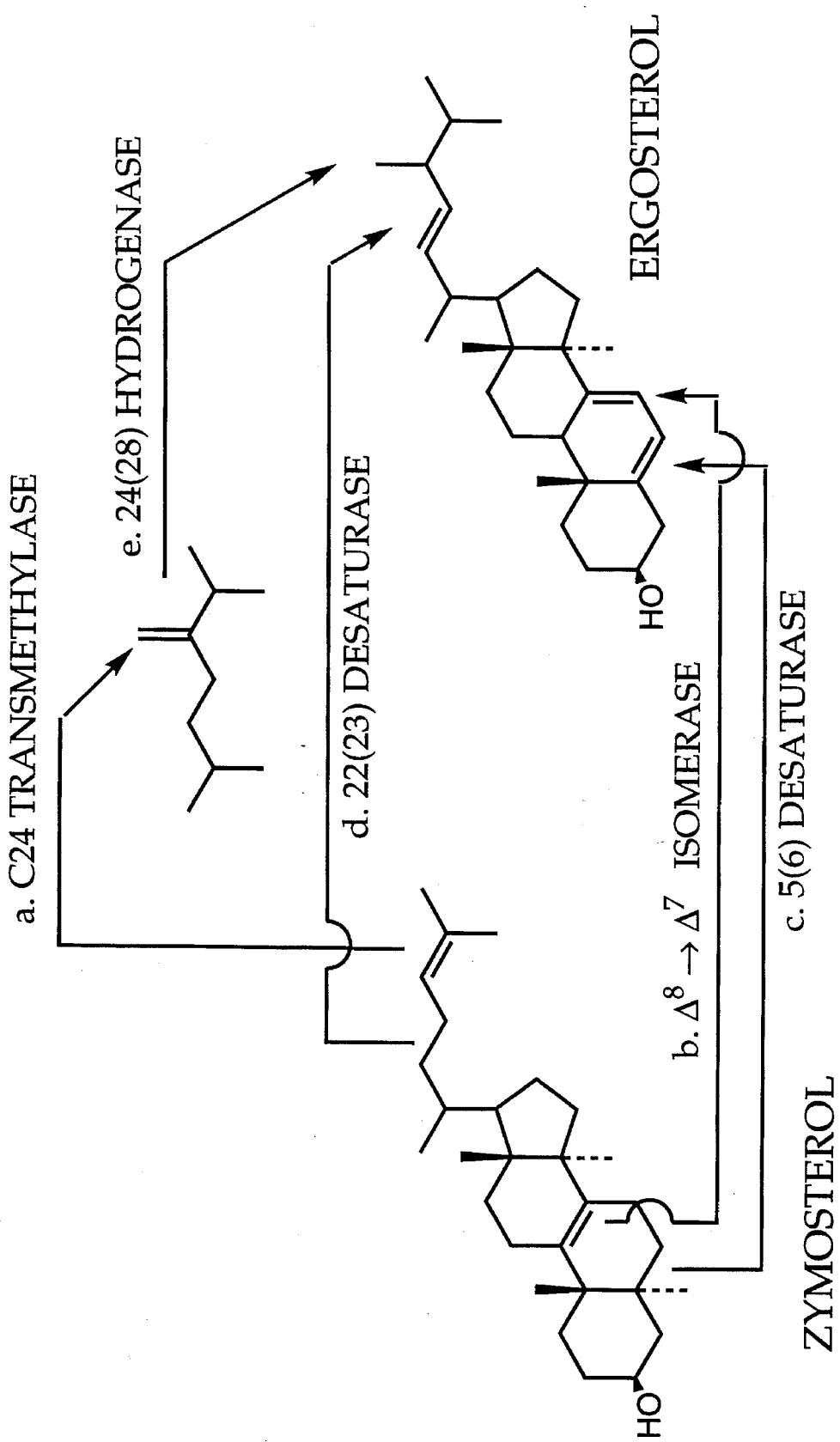

The following words and phrases have the meanings set forth below.

Expression: The combination of intracellular processes, including transcription and translation, undergone by a structural gene to produce a polypeptide.

Expression vector: A DNA sequence that forms control elements that regulate expression of structural genes when operatively linked to those genes.

Operatively linked: A structural gene is covalently bonded in correct reading frame to another DNA (or RNA as appropriate) segment, such as to an expression vector so that the structural gene is under the control of the expression vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecule: A hybrid DNA sequence comprising at least two nucleotide sequences not normally found together in nature.

Structural gene: A DNA sequence that is expressed as a polypeptide, i.e., an amino acid residue sequence.

Vector: A DNA molecule capable of replication in a cell and/or to which another DNA segment can be operatively linked so as to bring about replication of the attached segment. Alternatively, a vector can be a non-replicating vector that is integrated into the chromosome of the transformed cell. A plasmid is an exemplary vector.

II. The Invention

The present invention relates to compositions for modulating sterol compositions in yeast cultures as well as to the yeast that exhibit increased levels of specific sterol accumulation relative to a non-transformed yeast. Preferred yeasts are yeasts of the Saccharomvces or Candida genus. A more preferred yeast is *Saccharomyces cerevisiae* (*S. cerevisiae*).

The present invention relates to the isolation and characterization of the structural gene for Δ8-7 isomerase activity toward sterols in yeasts (ERG2), including the controlling and structural regions of the gene from *S. cerevisiae*. The structural gene is further defined to include a particular DNA sequence plus variants and analogs of the gene.

As contemplated herein, a structural gene of the invention is defined to include DNA segments that hybridize non-randomly with the structural gene for Δ8-7 isomerase of *S. cerevisiae* under stringency conditions as described herein. Thus, the gene of the invention encodes for Δ8-7 isomerase activity toward sterols, includes non-randomly-hybridizable variant or analog DNA segments, and produces biologically active polypeptides when expressed in a suitable host.

Polynucleotide hybridization is a function of sequence identity (homology), G+C content of the sequence, buffer salt content, sequence length and duplex melt temperature (Tm) among other variables. See, Maniatis et al., *Molecular Cloning*, Cold Spring Harbor Laboratory, Cold Spring Harbor, N.Y. (1982), page 388.

With similar sequence lengths, the buffer salt concentration and temperature provide useful variables for assessing sequence identity (homology) by hybridization techniques. For example, where there is at least 90 percent homology, hybridization is carried out at 68° C. in a buffer salt such as 6XSCC diluted from 20XSSC [Maniatis et al., above, at page 447]. The buffer salt utilized for final Southern blot washes can be used at a low concentration, e.g., 0.1XSSC and at a relatively high temperature, e.g., 68° C., and two sequences will form a hybrid duplex (hybridize). Use of the above hybridization and washing conditions together are defined as conditions of high stringency or highly stringent conditions.

Moderately high stringency conditions can be utilized for hybridization where two sequences share at least about 80 percent homology. Here, hybridization is carried out using 6XSSC at a temperature of about 50°–55° C. A final wash salt concentration of about 1–3XSSC and at a temperature of about 60°–68° C. are used. These hybridization and washing conditions define moderately high stringency conditions.

Low stringency conditions can be utilized for hybridization where two sequences share at least 40 percent homology. Here, hybridization is carried out using 6XSSC at a temperature of about 40°–50° C., with a final wash buffer salt concentration of about 6XSSC at a temperature of about 40°–60°C. These hybridization and washing conditions define low stringency conditions.

An isolated DNA or RNA segment that contains a nucleotide sequence that is at least 80 percent, and more preferably at least 90 percent identical to a DNA sequence for Δ8-7 isomerase shown in FIG. 2 (SEQ ID NO:1) is contemplated by this invention. Such a nucleotide sequence, when present in a host cell as part of a plasmid or integrated into the host genome as described herein, that also hybridizes non-randomly under at least moderately high stringency conditions and expresses a biologically active Δ8-7 isomerase is contemplated herein as a variant of the illustrated sequence that exhibits substantially the same biological activity.

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence; i.e., protein or polypeptide, for which it codes.

Thus, through the well-known redundancy of the genetic code, additional DNA and corresponding RNA sequences can be prepared that encode the same amino acid residue sequences, but that are sufficiently different from an identified gene sequence that the two sequences do not hybridize at high stringency, but do hybridize at moderately high stringency. Furthermore, allelic variants of a structural gene can exist in other strains that are also useful, but form hybrid duplex molecules only at moderately high stringency.

A DNA or RNA sequence that (1) encodes an enzyme molecule exhibiting substantially the same biological activity as a Δ8-7 isomerase expressed by a DNA sequence of FIG. 2, (2) hybridizes with a DNA sequence of the structural gene in the figure at least at moderately high stringency and (3) shares at least 80 percent, and more preferably at least 90 percent, identity with the ONA sequence of the structural gene in the figure is defined as a DNA variant sequence.

Analog or analogous ONA and RNA sequences that encode the above enzyme proteins are also contemplated as part of this invention. A DNA and RNA sequence that encodes an amino acid residue sequence that is at least 40 percent, and more preferably at least 80 percent, and most preferably at least 90 percent, identical to that of an Δ8-7 isomerase polypeptide shown in FIG. 2, herein under low stringency hybridization conditions but not at moderately high stringency are also contemplated, and are referred to herein as an "analog of" or "analogous to" a DNA sequence shown in a figure. A polynucleotide that encodes an analogous sequence must also produce a functional or biologically active Δ8-7 isomerase upon expression in a suitable host.

As contemplated by this invention, yeasts may be transformed with an added structural gene that encodes a polypeptide having Δ8-7 isomerase activity, that encoded polypeptide being expressed in the transformed yeast, or in combination with previously introduced HMG-CoA reductase genes encoding polypeptides having HMG-CoA reductase activity. Preferred non-transformed yeasts are mutant species having a single or double defect in the expression of enzymes involved in converting zymosterol to ergosterol (sterol biosynthetic pathway enzymes). The non-transformed and transformed yeasts compared are of the same species, such as S. cerevisiae.

Modulation of sterol distribution in a yeast culture is accomplished by increasing the cellular activity of the enzyme Δ8-7 isomerase. Overall sterol production has been shown to be increased by increasing the cellular activity of the enzyme HMG-CoA reductase, which enzyme catalyzes the conversion of 3-hydroxy-3-methylglutaryl Coenzyme A (HMG-CoA) to mevalonate. (See copending U.S. patent application No. 07/783,861, which is hereinafter incorporated by reference. As used herein, "cellular activity" refers to the total catalytic activity of Δ8-7 isomerase or HMG-CoA reductase in a yeast cell).

Cellular Δ8-7 isomerase activity is increased by increasing the expression level of a structural gene encoding a polypeptide having Δ8-7 isomerase catalytic activity. Expression of that encoded structural gene enhances the cellular activity of that enzyme. The expression level is increased by methods well known in the art. For example, expression of a structural gene is increased by deregulating the promoter, which controls expression of such a structural gene. The promoter that regulates expression of the Δ8-7 isomerase gene in a normal, wild-type yeast can be identified and excised from the genome. A new promoter, which allows for overexpression of the Δ8-7 isomerase gene, is then inserted according to standard transformation techniques. A preferred means of increasing the expression level of a structural gene encoding a polypeptide having Δ8-7 isomerase catalytic activity is to increase the copy number of a structural gene encoding such a polypeptide.

The copy number is increased by transforming a yeast cell with a recombinant DNA molecule comprising a vector operatively linked to an exogenous DNA segment that encodes a polypeptide having Δ8-7 isomerase activity, and a promoter suitable for driving the expression of said polypeptide in said yeast. Such a polypeptide is catalytically active, and is preferably a complete Δ8-7 isomerase protein. Thus, a transformed yeast cell has one or more added genes that encode a polypeptide having Δ8-7 isomerase activity relative to a non-transformed yeast of the same species. As such, a transformed yeast can be distinguished from a non-transformed yeast by standard technology such as agarose separation of DNA fragments or mRNAs followed by transfer and appropriate blotting with DNA or RNA or by use of polymerase chain reaction technology, as are well known. Relative Δ8-7 isomerase activity of the transformed and non-transformed yeasts can also be compared, with a relative increase in Δ8-7 isomerase activity in transformed yeasts being indicative of transformation.

The accumulation of specific sterols can also be used to distinguish either between non-transformed and transformed yeasts, or yeasts previously transformed with HMG-CoA reductase and newly transformed with Δ8-7 isomerase, for example.

A. Structural Genes

The present invention contemplates a structural gene that encodes a polypeptide having Δ8-7 isemerase activity. The Δ8-7 isomerase enzymes of yeast cells comprise distinct amino acid residue sequence regions, which regions are designated the catalytic region and the putative membrane associating region.

The catalytic region contains the active site of the Δ8-7 isomerase enzyme and comprises about ninety percent of the total, localized on the COOH-terminal portion of the Δ8-7 isomerase enzyme. The putative membrane associating region contains hydrophobic amino acid residues and comprises about ten percent of the total, localized on the $NH_2$-terminal portion of the Δ8-7 isomerase enzyme.

The structural gene encoding for the Δ8-7 isomerase of S. cerevisiae can be obtained by the methods described by Ashman et al., Lipids, Vol. 26, No. 8 (1991). Other methods are described in Examples 1 and 2 herein.

In a preferred embodiment, the utilized structural gene encodes the catalytic region and at least a portion of the membrane associating region of Δ8-7 isomerase.

Yeast cells contain one gene encoding Δ8-7 isomerase, designated ERG2. The nucleotide base sequence of ERG2 (SEQ. I.D. No. 1) for S. cerevisiae as well as the amino acid sequence of the corresponding Δ8-7 isomerase (SEQ ID No: 2) are presented in FIG. 2.

The ERG2 structural gene comprises about 669 base pairs. Intact Δ8-7 isomerase comprises a core amino acid sequence of about 222 amino acid residues.

The catalytic region of Δ8-7 isomerase comprises amino acid residues from about residue 22 to about residue 222: i.e., the COOH-terminus. A structural gene that encodes the catalytic region comprises bases from about nucleotide position 63 to about position 666 of FIG. 2 (SEQ. I.D. No. 1).

The putative membrane associating region of Δ8-7 isomerase comprises an amino acid sequence from about residue 1 to about residue 21. A gene region that encodes the membrane associating region of the enzyme comprises nucleotides from about position 1 to about position 63 of FIG. 2 (SEQ. I.D. No.1). A structural gene encoding a polypeptide comprising the catalytic region and at least a portion of the membrane associating region of yeast Δ8-7 isomerase preferably comprises the structural gene encoding the membrane association region of the enzyme operatively linked to the structural gene encoding the catalytic region of the enzyme.

For strains of yeast having both HMG CoA reductase and Δ8-7 isomerase, a construct similar to those above from an analogous portion of yeast HMG-CoA reductase 2 can also be utilized.

The previously described DNA segments are noted as having total overall lengths. However, a minimal length defines the length of a DNA segment having a sequence that encodes a particular polypeptide having Δ8-7 isomerase activity. As is well known in the art, so long as the required DNA sequence is present and in proper reading frame, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, the maximum size of a recombinant DNA molecule, particularly an expression vector, is governed mostly by convenience and the vector size that can be accommodated by a host cell, once all of the minimal DNA sequences required for replication and expression, when desired, are present. Typically, a DNA segment of the invention can be up to 15,000 base pairs in length. Minimal vector sizes are well known.

B. Recombinant DNA Molecules

A structural gene of the present invention can be incorporated into a recombinant DNA molecule by operatively linking a vector to a useful DNA segment to form a plasmid such as discussed herein. A vector capable of directing the expression of a polypeptide having Δ8-7 isomerase activity is referred to herein as an "expression vector".

Such expression vectors contain expression control elements including the promoter. The polypeptide coding genes are operatively linked to the expression vector to permit the promoter sequence to direct RNA polymerase binding and expression of the desired polypeptide coding gene. Useful in expressing the polypeptide coding gene are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as disclosed in Chau et al., *Science*, 244:174–181 (1989). The promoter preferably comprises a promoter sequence whose function in regulating expression of the structural gene is substantially unaffected by the amount of sterol in the cell. As used herein, the term "substantially unaffected" means that the promoter is not responsive to direct feedback control by the sterols accumulated in transformed cells.

A promoter is also selected for its ability to direct the transformed yeast's transcriptional activity to the structural gene encoding a polypeptide having Δ8-7 isomerase activity. Structural genes can be driven by a variety of promoters in yeast.

Promoters utilized with the present invention are those preferably regulated by factors, which can be monitored and controlled in the internal or external environment of the transformed cell. Examples of promoters inducibly regulated by factors in the cell's external environment (extrinsic factors) are the well known GAL 1 promoter, the GAL 10 promoter, the GAL 1–10 promoter, the GAL 7 promoter, the metallothionine promoter, the a-factor promoter, the invertase promoter and the enolase promoter. Preferred are the well known GAL 1, the GAL 10 and the GAL 1–10 promoters.

Examples of promoters subject to inducible regulation by factors in the cell's internal environment (intrinsic factors) are the well known phosphoglycerate kinase (PGK) promoter, the triose-phosphate isomerase (TPI) promoter, the alcohol dehydrogenase (ADH) promoter and the repressible acid phosphatase promoter. Preferred are the well known PGK and the ADH promoters.

The choice of which expression vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene included in the DNA segment to which it is operatively linked.

The present method contemplates a plasmid vector. The plasmid vectors of the present invention can be incorporated either within (integrated) or without (episomal) the chromosomes of the transformed cell. An episomal plasmid includes an origin of replication for yeast, the nucleic acid sequence that encodes a polypeptide having Δ8-7 isomerase activity, a promoter, and a selective marker. The selective marker can include genes conveying antibiotic resistance, or permitting an auxotrophic host to metabolize a substrate that it would not otherwise be able, but for the presence of the plasmid vector. However, the use of antibiotic resistance as a selective marker requires growing organisms in an antibiotic culture media. Due to the expense of the antibiotic, organisms dependent on antibiotics are difficult to develop commercially. Generally, auxotrophic organisms are used for yeast.

Auxotrophic organisms can be produced by mutation and culture techniques which are well known in the art. Selective markers which can complement an auxotrophic host organism include the well known TRP 1 gene encoding phosphoribosyl anthraniline isomerase, the URA 3 gene encoding orotine-5' phosphate decarboxylate, the LEU 2 gene encoding isopropylmalate isomerase, and the HIS 3 gene encoding histidinol dehydrogenase.

Episomally replicating vectors are sometimes difficult to maintain in host organisms for long periods of time in liquid culture, especially when the selective pressure used to maintain the vector is complementation of a nutritional auxotrophy. A preferred vector includes an integrating vector which requires little or no selective pressure to maintain base sequences for the polypeptide having Δ8-7 isomerase activity and the promoter.

Integrating vectors, in accordance with the present invention, include base sequences that encode a polypeptide having Δ8-7 isomerase activity, a promoter, a selective marker and sequences homologous to host chromosomal DNA that permit the base sequences to be incorporated within the chromosome via homologous recombination. The homologous region includes restriction sites that permit the plasmid to become linear. In linear form, the plasmid can recombine at homomogous regions of the chromosome. Integrating vectors do not include odgins of replication for the host organism.

Individuals skilled in the art will readily recognize that episomal and integrating vectors are often amplified in organisms other than the intended host and require means of replication and selection in the non-host organism. Generally, the non-host organism is *Escherichia coli* due to its well-known features and characteristics.

In preferred embodiments, the vector used to express the polypeptide coding gene includes a selection marker that is effective in a yeast cell, such as the URA 3 or TRP I markers. Other suitable selection means for use in amplifying the vectors in bacteda include antibiotic markers, such as genes encoding for beta lactamase (penicillin resistance), chloramphenicol transacetylase (chloramphenicol resistance), and neomycin phosphotransferase (kanamycin and neomycin resistance).

As is well-known in the art, numerous methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

C. Transformed Yeasts and Methods Of Transformation

The structural gene of the present invention can be transformed into a yeast. The copy number of a gene coding for a polypeptide having Δ8-7 isomerase activity is increased by transforming a desired yeast with a suitable vector that contains that structural gene. Expression of that gene in the transformed yeast enhances the activity of Δ8-7 isomerase.

Yeast cells are transformed in accordance with the present invention by methods known and readily apparent to those of skill in the yeast transformation art, [See, e.g., Hinnen et al., *Proc. Natl. Acad. Sci. USA*, 75:1929-(1978); Ito et al., *Bact.*, 5:163–168 (1983)].

A preferred general method of transformation is the lithium acetate procedure of Ito et al., above. Yeast cells are grown to a concentration of about $2\times10^7$ cells/ml in a medium containing yeast extract, bactopeptone and dextrose. Cells are collected by low speed centrifugation and resuspended in a transformation medium containing tryptone, yeast extract, NaCl and lithium acetate.

Cells are maintained in the transformation medium for about 1 hour at about 30° C. Recombinant DNA molecules of desired composition are added to the transformation medium cell suspension and the mixture is stirred constantly at about 30° C. for about 1 to 1.5 hours. Polyethyleneglycol (M.W. 4000) is then added to the cell suspension such that the final concentration of polyethyleneglycol is about 35% weight/volume (w/v). Cells are maintained in the polyethyleneglycol-containing solution at about 30° C. for about 2 hours and then at about 42° C. for an additional 5 minutes. Sterile distilled water is added to the cell suspension, and the cells collected by low speed centrifugation. Further specifics are provided hereinafter.

Successfully transformed cells are identified by growing the transformed cells on selection medium, identifying cell characteristics indicative of transformation (i.e., increased accumulation of squalene or specific sterols), analyzing nucleic acids isolated from such transformed cells with standard techniques such as Southern Blot analysis, [Holm, C. et al., *Gene*, 42:169 (1986)].

D. Mutated Yeasts

The yeasts utilized in accordance with the present invention are mutated yeasts having single or double defects in the expression of enzymes that catalyze the conversion of zymosterol to ergosterol. Such enzymes are referred to herein as "erg" gene products. Table 3 below lists the particular erg designations for specific enzyme expression defects utilized in the present invention.

TABLE 3

| Enzyme Expression Defect | Mutant Designation |
| --- | --- |
| zymosterol-24-methyltransferase | erg6 |
| ergosta-5,7,24(28)-trienol-22-dehydrogenase | erg5 |
| Δ8-7 isomerase | erg2 |

Mutants used in accordance with tile present invention can be purchased or generated from commercially available sources such as the Yeast Genetic Stock Center (Berkeley, Calif.). For example, erg5 and erg5-erg6 double mutants are produced from commercially available sources.

Mutants are also obtained by well known methods of inducing mutations. See, e.g., Boeke, J. D. et al., *Mol. Gen. Genet.*, 197:345–346 (1984); Rose, M. D. et al., *Methods in Yeast Genetics*, Cold Spring Harbor Laboratory, N.Y. (1990).

Mutants having single expression defects are then crossed to generate mutants having double defects in enzyme expression. For example, the crossing of mutant ATC6118 with mutant ATC0501 yields mutant ATC6119, an erg3-erg6 double mutant.

E. Sterol Accumulation in Transformed Yeast

The ERG2 transformed mutant erg2 yeast species of the present invention accumulate relatively normal sterols relative to non-transformed mutants of the same species. That is, an erg2 mutant transformed with a plasmid vector such as pARCml508 accumulates ergosterol.

Relative to a non-transformed erg5-erg6 mutant, an erg5-erg6 double mutant transformed with the plasmid vector useful herein does not greatly overaccumulate the characteristic intermediates squalene, zymosterol, cholesta-5,7,24-trienol and cholesta-7,24-dienol. It does, however, change the ratio of zymosterol to cholesta-5,7,24-trienol and cholesta-7,24-dienol from about two to one, to one to one.

F. Sterol Δ8-7 Isomerase (ERG2) Activity In Transformed Yeasts

The expression of a structural gene encoding a polypeptide having ERG2 activity in the transformed yeast of the present invention enhances the cellular activity of ERG2. As a result of transformation, the copy number of an added gene encoding a polypeptide having ERG2 activity is increased from 1 to about 2 to about 4.

Cellular activity of ERG2 in such transformed cells is proportional to the increase in copy number. Thus, when the copy number is increased to about 2, ERG2 activity is elevated to a level about 3 times the activity observed in non-transformed yeast. However, a further increase in the copy number to a level of about 4 is not accompanied by a further increase in ERG2 activity.

G. Harvesting of Sterols

If desired, transformed yeasts are harvested to recover the sterol product. Most of the sterol in these genetically transformed yeasts occurs in the form of fatty acid esters. To obtain free sterols, it is therefore necessary to saponify the "yeast pulp" in base, e.g., as described in the sterol and analysis section (2:1 EtOH/$H_2O$ containing 20% w/v KOH).

In a preferred embodiment, harvesting comprises:

(i) homogenizing sterol-containing transformed yeasts to produce a pulp; and (ii) extracting the sterol(s) from the pulp with an appropriate basic solvent such as an organic solvent or by supercritical extraction followed by base saponification in an appropriate solvent [Favati et al., *J. Food Sci.*, 53:1532 (1988) and the citations therein] to produce a sterol-containing liquid solution or suspension; and (iii) isolating the sterol(s) from the solution or suspension.

Transformed yeasts are homogenized to produce a pulp using methods well known to one skilled in the art. This homogenization can be done manually, by a machine, or by a chemical means. The pulp consists of a mixture of the sterol of interest, residual amounts of precursors, cellular particles and cytosol contents, which is subjected to extraction procedures.

Sterol(s) can be extracted from the pulp produced above to form a sterol-containing solution or suspension. Such extraction processes are common and well known to one skilled in this art. For example, the extracting step can consist of soaking or immersing the pulp in a suitable solvent. This suitable solvent is capable of dissolving or suspending the sterol present in the pulp to produce a sterol-containing solution or suspension. Solvents useful for such and extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction.

Yeasts transformed with a structural gene for an active Δ8-7 isomerase enzyme are grown under suitable culture conditions for a period of time sufficient for sterols to be synthesized. The sterol-containing yeast cells are then lysed chemically or mechanically, and the sterol is extracted from the lysed cells using a liquid organic solvent, as described before, to form a sterol-containing liquid solution or suspension. The sterol is thereafter isolated from the liquid solution or suspension by usual means such as chromatography.

The sterol is isolated from the solution or suspension produced above using methods that are well known to those skilled in the art of sterol isolation. These methods include, but are not limited to purification procedures based on solubility in various liquid media chromatographic techniques such as column chromatography and the like.

EXAMPLES

The following examples illustrate the invention and are not to be construed as limiting the invention or claims in any way.

Example I. Isolation of the Erg2 Structural Gene

A. Isolation of the Plasmid pARCml500

A YEP13 based library containing inserts from *S. cerevisiae* DNA was obtained from ATCC (Rockville, Md., ATCC cat. no. 37,323, 2d Edition. 1991). The library was received in the form of transformed *E. coil* cells. The cells were grown in LB medium (500 ml, 37° C.) overnight containing 100 μg/ml ampicillin. The cells were harvested and the plasmids contained therein were harvested. The plasmids contained therein were extracted and purified in accordance with standard procedures [Maniatis].

The purified library DNA was then used to transform an erg2leu2 strain of *S. cerevisiae* according to the method of Ito. The putative transformed yeast cells were selected on SD-leucine media. Those colonies that grew on the selected media were pooled and diluted into SD-medium at ratios of 1:500 and 1:5000. The diluted yeast cells were replated onto SD-leucine plates. After overnight growth, the cells were replica plated onto SD-leucine containing 50 μg/ml Nystatin and allowed to grow for 2 days. Patterns of growth on the SD-leu and SD-leu plus Nystatin plates were compared. Cells that did not grow on Nystatin were picked for further analysis.

Colonies displaying a Nystatin sensitive phenotype were analyzed for sterol composition using gastromatography-masspectrometry (GC-MS) as follows. Fifty to one hundred mg of lyophilized yeast cells were extracted/saponified in 10 ml of an ethanol/water (2:1) solution containing 20% (W/V) KOH for two hours at 80° C. Extracts were partially neutralized with 10 ml 1N HCl and extracted twice with 15 ml n-heptane. The sterol-containing heptane fractions were evaporated to dryness under a stream of nitrogen gas and resuspended to an appropriate volume with heptane containing an internal standard (5-alpha-cholestane). The resuspended samples were analyzed for sterol accumulation by capillary GC with flame ionization detection and GC-MS.

Cells found to contain ergosterol were then grown for extraction of the transforming plasmid. Extraction of the plasmids from yeast was performed by using conventional procedures. (c.f., Methods in Yeast Genetics, A Laboratory Course Manual, Rose et al., Cold Spring Harbor Press, Cold Spring Harbor, N.Y. ((1990), p, 130.)

Plasmids isolated from putative Erg2 gene transformants were reintroduced into Erg2leu2 yeast strains for confirmation of the phenotype as described above.

A plasmid conferring complementation of the erg2 phenotype was designated pARCml500.

Mapping the Plasmid pARCml500

Restriction site location for pARCml500 were determined using the restriction enzymes EcoRV, Kpnl, Xbal, Sacl, Accl, Hind III, Bam Hl, Sphl and, Xhol. Mapping was accomplished by digesting samples of the plasmid singly or with combinations of the above named enzymes.

Location of the Erg2, Structural Gene

Fragments containing portions of the original pARCml500 insert DNA were subcloned into standard yeast vectors capable of selection by chromogenic indicators (e.g., β-galactosidase, β-glucuranidase) and *E. coil* transcription vectors pGEM™-3 and pGEM™-4 available from Promega Biotech (Madison, Wisc.). Other suitable yeast vectors are described by Sikorski, Genetics, 122, 19–27 (May 1989) and Gietz, GENE 74, 527–534 (1988).

Figure 3:
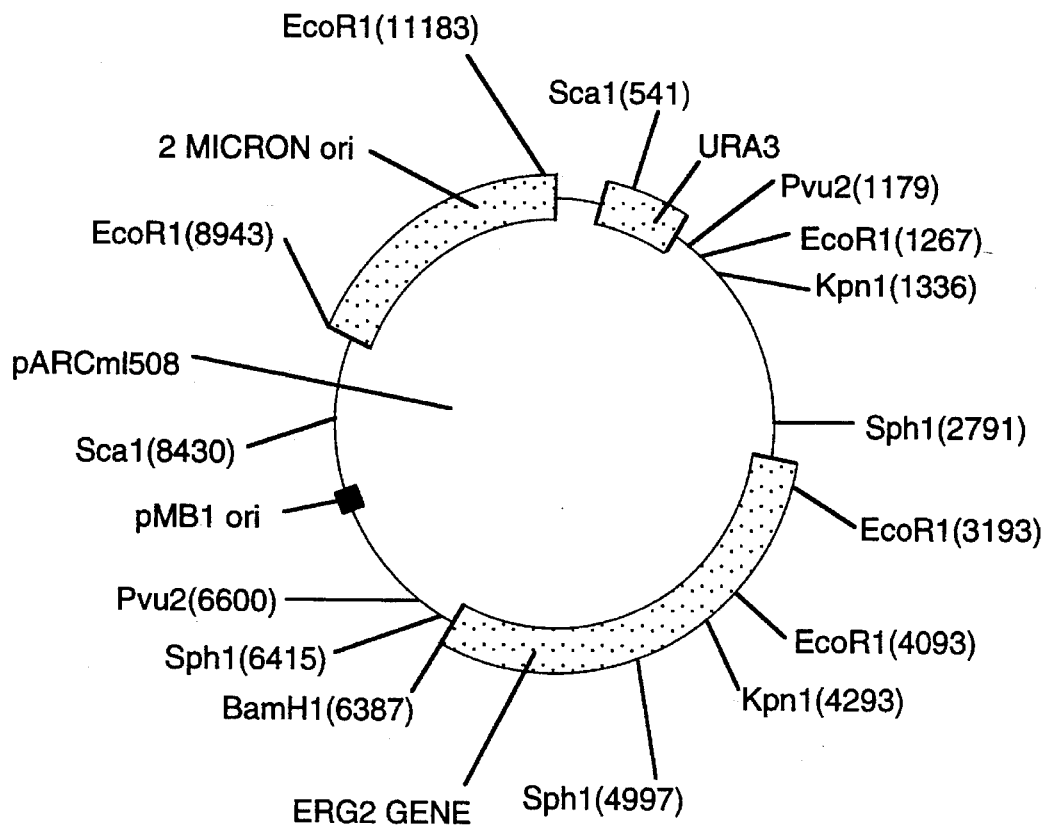

Subclones in yeast vectors were transformed into erg2 strains to test for complementation by the methods described above. By comparison of the subclones which conferred Erg2 activity, the location of the erg2 gene was determined. The erg2 gene was located between the BamHl and Sphl site as shown on the map for pARCml508 shown in FIG. 3. Plasmid pARCml508 was deposited with the ATCC, 12301 Parklawn Drive, Rockville, Md. 20852 under the terms of the Budapest Treaty on Jan. 12, 1993, and has received accession number ATCC 75396.

The BamHl-Sphl fragment was further analyzed by restriction mapping in preparation for direct sequence analysis. Restriction sites for Ndel, Scal, Ncol and Spel yielded a usable distribution of sites for further subcloning and direct sequence analysis. Nucleotide sequences were determined by the method cf Sanger. Subclones containing the fragments from the above described digests were placed into pGEM$^R$-5 ZF (+) and pGEM-72f(+) (Promega Biotech, Madison, Wisc.), Primers for sequencing were obtained from Promega Biotech for use with pGEM$^R$-5 ZF(+) and used in accordance with the manufacturer's directions. Sequencing of regions internal to the known restriction sites was accomplished using primers obtained directly from the just determined nucleotide order. Altogether, a sequence for a region comprising about 1460 contiguous bases was obtained. This determined the erg2 structural gene region.

The precise location of the erg2 transcribed region was obtained by the method of primer extension [Maniatis]. RNA was obtained for the primer extension experiments by the method of Sherman. The transcribed region comprised approximately 900 bases and corresponded to a deduced open reading frame (ORF) of about 670 bases as depicted in FIG. 2.

EXAMPLE 2

Isolation of Δ8-7 isomerase gene from *S. Cererisiae by Complementetlon of an erg2 Mutant.*

In order to perform genetic crosses it is advantageous to have "markers" comprising easily identifiable physical or biochemical characteristics. This was accomplished with an erg2 yeast strain (generously provided to the inventors by Martin Bard of Purdue University Medical School) by the method described in Methods in Yeast Genetics, Cold Spring Harbor Press. Briefly, the method involves the following: The erg2 strain was grown in YEPD media overnight. A 10 ml. quantity of the yeast culture containing about 5×10$^8$ cells was pelleted by centrifuging at 5000 rpm for 10 min. The supernatant was discarded, and the yeast pellet resuspended in 1.5 ml sodium phosphate buffer. A 50 μl quantity of ethyl methyl sulfonate (EMS- Sigma Chemicals) was added, and the mixture was placed on a rotary shaker. After 1 hour of shaking at 30° C., 10 ml of 5% sodium thiosulphate was added, and the mixture incubated for 15 min. at room temperature (ca. 25° C.). The mixture was centrifuged for 10 min at 5000 rpm to pellet the cells, which were then resuspended in 50 ml. of YEPD media and grown overnight. The following morning, the cells were diluted to various concentrations, placed on YEPD plates, and incubated until small colonies were formed. The colonies were replicaplated onto minimal growth media (SD), and those colonies exhibiting a growth deficiency were further analyzed. An erg2 adenine mutant was chosen for further experimentation.

Yeast of the species *S. cerevisiae* were transformed in accordance with a lithium acetate procedure, [Ito, H. et al., *Bact.*, 5:163–168 (1983)]. Yeast cells were grown in about 50 ml of YEPD medium (yeast extract 1% w/v, bactopeptone, 2% w/v: and dextrose, 2% w/v) overnight at about 30° C. When the concentration of cells was about 2×10$^7$ cells/ml, the cells were collected by low speed centrifugation. Cells appearing in the pellet of the centrifugation were suspended in about 15 ml of TYE medium (tryptone, 5 g/l; yeast extract, 10 g/l and NaCl, 5 g/l) and repelleted by centrifugation. The pellet from this second centrifugation was resuspended in about 50 ml of TYE buffer containing 0.1M lithium acetate (LiOAc) and the suspension maintained at about 30° C. for one hour with constant shaking.

A YEp13 yeast DNA library obtained from American Type Culture Collection (ATCC catalog #37,323, 2d Edition, 1991) was used to transform the yeast erg2 mutant. DNA (about 100 mg in 1.4 ml of TBE buffer) was added to the TYE-LiOAc suspension and the admixture maintained at about 30° C. for one to one and one-half hour with constant shaking. The DNA-containing cell suspension was then mixed with polyethyleneglycol (44% w/v) such that the final concentration of polyethyleneglycol (PEG) was about 35% (w/v).

The cells were maintained in this PEG solution at about 30° C. for about two hours and then at about 42° C. for about five minutes. About 10 ml of sterile, distilled water was added to each suspension and the cells were collected by low speed centifugation. Collected cells were dispersed in about 100 μl of distilled water and plated on selective medium.

Transformation of cells was confirmed by growth on selection medium, identification of cell characteristics indicative of transformation (i.e., increased levels of selected sterols or squalene), and Southern Blot analysis of nucleic acid isolated from such transformed cells, [Holm, C. et al., *Gene*, 42:169–173 (1986)].

We claim:

1. An isolated DNA segment comprising a nucleotide sequence that encodes *Saccharomyces cerevisiae* Δ8-7 isomerase, said isomer having the amino acid residue sequence shown in SEQ ID NO: 2.

2. The DNA segment of claim 1 that comprises at least about 669 base pairs that define a structural gene for the *Saccharomyces cerevisiae* Δ8-7 isomerase depicted as base pairs 379 to 1047 in SEQ ID NO: 1.

3. A vector comprising the DNA segment of claim 1.

4. A host cell comprising the vector of claim 3.

5. An isolated DNA segment comprising a nucleotide sequence that encodes a structural gene for the *Saccharomyces cerevisiae* Δ8-7 isomerase contained in the plasmid pARCml508.

6. Plasmid pARCml508 having ATCC accession number 75396.

7. An isolated DNA segment comprising a nucleotide sequence encoding a catalytic region for the Δ8-7 isomerase for *Saccharomyces cerevisiae*.

* * * * *